United States Patent
Orderud et al.

(10) Patent No.: US 8,265,363 B2
(45) Date of Patent: Sep. 11, 2012

(54) METHOD AND APPARATUS FOR AUTOMATICALLY IDENTIFYING IMAGE VIEWS IN A 3D DATASET

(75) Inventors: Fredrik Orderud, Trondheim (NO); Stein Rabben, Sofiemyr (NO); Hans Torp, Midtnorge (NO); Vidar Lundberg, Trondheim (NO)

(73) Assignee: General Electric Company, Schenectady, NY (US)

( * ) Notice: Subject to any disclaimer, the term of this patent is extended or adjusted under 35 U.S.C. 154(b) by 749 days.

(21) Appl. No.: 12/365,738

(22) Filed: Feb. 4, 2009

(65) Prior Publication Data

US 2010/0195881 A1    Aug. 5, 2010

(51) Int. Cl.
G06K 9/00 (2006.01)
G06K 9/36 (2006.01)
G06K 9/46 (2006.01)

(52) U.S. Cl. ........ 382/128; 382/154; 382/160; 382/209; 345/420

(58) Field of Classification Search .................. 382/128, 382/154, 160, 209; 345/419, 420
See application file for complete search history.

(56) References Cited

U.S. PATENT DOCUMENTS

| | | | |
|---|---|---|---|
| 5,768,413 A * | 6/1998 | Levin et al. | 382/173 |
| 6,488,629 B1 | 12/2002 | Saetre et al. | |
| 6,500,123 B1 | 12/2002 | Holloway et al. | |
| 7,366,334 B2 * | 4/2008 | Yokota et al. | 382/128 |
| 7,428,334 B2 * | 9/2008 | Schoisswohl et al. | 382/173 |
| 7,558,402 B2 * | 7/2009 | Zhou et al. | 382/103 |
| 7,889,912 B2 * | 2/2011 | Orderud | 382/154 |
| 7,965,869 B2 * | 6/2011 | Zhou et al. | 382/103 |
| 2003/0006984 A1 * | 1/2003 | Gerard et al. | 345/424 |
| 2004/0264778 A1 * | 12/2004 | Liang et al. | 382/203 |
| 2005/0002556 A1 * | 1/2005 | Kaus et al. | 382/154 |
| 2005/0063581 A1 * | 3/2005 | Viala et al. | 382/154 |
| 2005/0147303 A1 * | 7/2005 | Zhou et al. | 382/190 |
| 2006/0045347 A1 * | 3/2006 | Xiao et al. | 382/190 |
| 2006/0056698 A1 * | 3/2006 | Jolly et al. | 382/190 |
| 2006/0064007 A1 * | 3/2006 | Comaniciu et al. | 600/416 |
| 2006/0078194 A1 * | 4/2006 | Fradkin et al. | 382/154 |
| 2006/0110037 A1 * | 5/2006 | Kaus et al. | 382/173 |
| 2006/0251304 A1 * | 11/2006 | Florin et al. | 382/128 |
| 2006/0253024 A1 * | 11/2006 | Altmann et al. | 600/437 |
| 2007/0276225 A1 * | 11/2007 | Kaufman et al. | 600/416 |
| 2008/0069436 A1 * | 3/2008 | Orderud | 382/154 |
| 2008/0123927 A1 * | 5/2008 | Miga et al. | 382/131 |
| 2008/0194957 A1 * | 8/2008 | Hoctor et al. | 600/443 |
| 2008/0262814 A1 * | 10/2008 | Zheng et al. | 703/11 |

(Continued)

OTHER PUBLICATIONS

US Patent Application, Methods for Using Deformable Models for Tracking Structures in Volumetric Data, filed Mar. 18, 2008, U.S. Appl. No. 12/050,715, Lead Inventor: Fredrik Orderud.

(Continued)

*Primary Examiner* — John Lee

(74) *Attorney, Agent, or Firm* — The Small Patent Law Group; Dean D. Small

(57) ABSTRACT

A method is provided for automatically identifying image views in a three-dimensional dataset comprises accessing with a processor a three-dimensional dataset comprising a plurality of image frames and fitting with the processor at least one deformable model to at least one structure within each of the image frames. The method further comprises identifying with the processor at least one feature point within each of the image frames based on the at least one deformable model and displaying on a display at least one image view based on the at least one feature point.

20 Claims, 10 Drawing Sheets

U.S. PATENT DOCUMENTS

| | | | |
|---|---|---|---|
| 2009/0037154 A1* | 2/2009 | Ecabert et al. | 703/2 |
| 2009/0171201 A1* | 7/2009 | Olson | 600/438 |
| 2009/0226057 A1* | 9/2009 | Mashiach et al. | 382/128 |
| 2009/0238404 A1* | 9/2009 | Orderud et al. | 382/103 |
| 2009/0290772 A1* | 11/2009 | Avinash et al. | 382/130 |
| 2009/0292557 A1* | 11/2009 | Sirohey et al. | 705/3 |
| 2010/0123715 A1* | 5/2010 | Hansegard et al. | 345/419 |
| 2010/0195881 A1* | 8/2010 | Orderud et al. | 382/131 |

OTHER PUBLICATIONS

US Patent Application, Methods and Apparatus for 4D Data Acquisition and Analysis in an Ultrasound Protocol Examination, filed Oct. 16, 2007, U.S. Appl. No. 11/873,182, Lead Inventor: Vidar Lundberg.

Xiaoguang Lu et al., Autompr: Automatic Detection of Standard Planes in 3D Echocardiography, Siemens Corporate Research, Princeton, USA, Siemens Medical Solutions, Mountain View, USA, 978-1-4244-2003-2/08/$25.00 © 2008 IEEE, ISBI 2008, (4) pages.

D. Doo and M. Sabin, Behaviour of Recursive Division Surfaces Near Extraordinary Points, 0010-3385.78.0603056--05 $02.00 © 1978 IPC Business Press, vol. 10, No. 6, Nov. 1978, (7) pages.

K.Y.E. Leung et al., Sparse Registration for Three-Dimensional Stress Echocardiography, IEEE Transactions on Medical Imaging, vol. 27, No. 11, Nov. 2008, (12) pages.

M. Van Stralen et al., Time Continuous Detection of the Left Ventricular Long Axis and the Mitral Valve Plane in 3-D Echocardiography, Ultrasound in Med. & Biol., vol. 34, No. 2, pp. 196-207, 2008.

F. Veronesi et al., Tracking of Left Ventricular Long Axis From Real-Time Three-Dimensional Echocardiography Using Optical Flow Techniques, IEEE Transactions on Information Technology in Biomedicine, vol. 10, No. 1, Jan. 2006, (8) pages.

L. Sugeng et al., Left Ventricular Assessment Using Real Time Three Dimensional Echocardiography, Heart 2003; 89 (Suppl. III); pp. 29-36, www.heartjnl.com.

Fredrik Orderud and Stein Inge Rabben, Real-Time 3D Segmentation of the Left Ventricle Using Deformable Subdivision Surfaces, 978-1-4244-2243-2/08/$25.00 © 2008 IEEE.

* cited by examiner

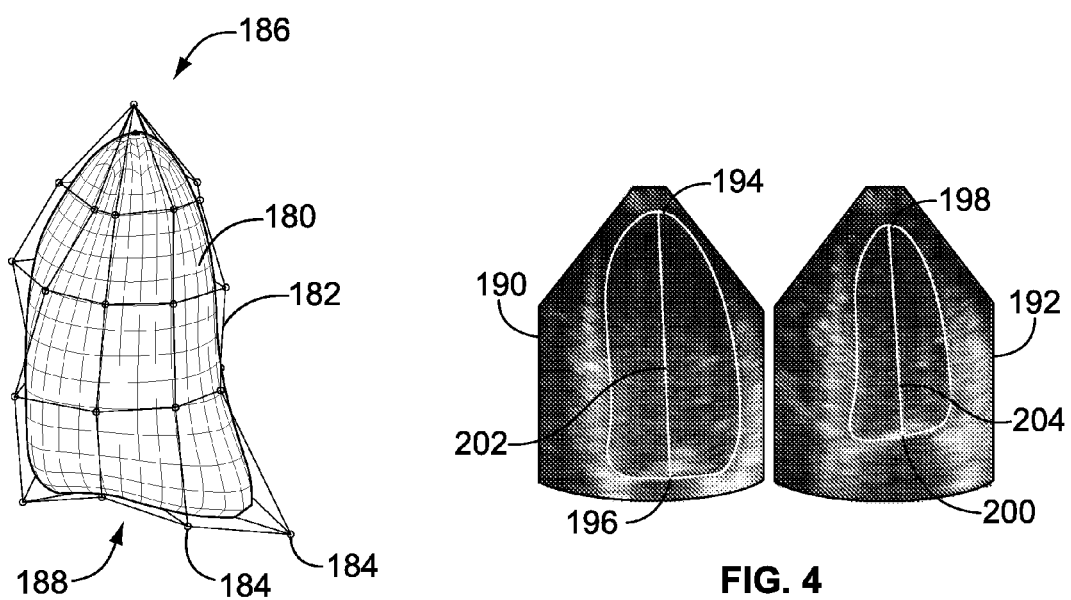
FIG. 3
FIG. 4
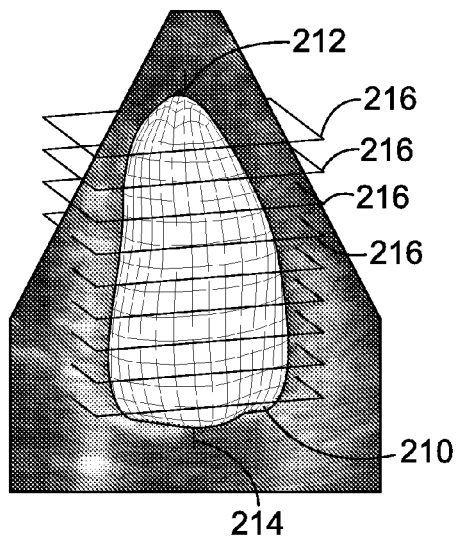
FIG. 5

METHOD AND APPARATUS FOR AUTOMATICALLY IDENTIFYING IMAGE VIEWS IN A 3D DATASET

BACKGROUND OF THE INVENTION

This invention relates generally to ultrasound and more particularly to automatically identifying image views from within a three-dimensional (3D) dataset.

Numerous tools for quantitative analysis of 3D echocardiograms are available. In particular, assessment of the left ventricle is of interest. With 3D echocardiography, arbitrary image slices may be extracted from acquired volumes, which may be acquired as a series of image frames covering the cardiac cycle. Some level of input from the user is needed, however. For example, existing tools require manual alignment of the left ventricular long-axis, which increases examination time. Due to the time required, the user may identify the apex and base, that is, the top and bottom, of the heart on one image frame. These landmarks are then applied to the remaining image frames. Therefore, the remaining image frames or slices remain at fixed spatial positions within the image volume throughout the cardiac cycle.

The heart moves, however, during contraction, and thus the position of the heart moves within the image frames. Therefore, the myocardial tissue being displayed differs during the cardiac cycle. This is especially a problem for basal short-axis slices, where the longitudinal shortening may be up to 1.2 centimeters during the cardiac cycle. The resulting out-of-plane motion can give rise to artificial wall thickening unrelated to cardiac contraction, and basal slices can end up in the atria at end systole.

BRIEF DESCRIPTION OF THE INVENTION

In one embodiment, a method for automatically identifying image views in a three-dimensional dataset comprises accessing with a processor a three-dimensional dataset comprising a plurality of image frames and fitting with the processor at least one deformable model to at least one structure within each of the image frames. The method further comprises identifying with the processor at least one feature point within each of the image frames based on the at least one deformable model and displaying on a display at least one image view based on the at least one feature point.

In another embodiment, a system for automatically identifying image views in a three-dimensional dataset comprises a processor and a display. The processor is configured to access a three-dimensional dataset comprising a plurality of image frames, fit at least two coupled deformable models to structures within each of the image frames, and identify at least one feature point within each of the image frames based on at least one of the deformable models. The display is configured to display at least one image view based on the at least one feature point.

BRIEF DESCRIPTION OF THE DRAWINGS

FIG. 3 illustrates a Doo-Sabin subdivision model enclosed in a wire frame mesh that shows a plurality of control vertices in accordance with an embodiment of the present invention.

FIG. 4 illustrates exemplary segmented intersection slices at end diastole and end systole that have feature points identified thereon in accordance with an embodiment of the present invention.

FIG. 5 illustrates an example of identifying short axis slices based on feature points in accordance with an embodiment of the present invention.

DETAILED DESCRIPTION OF THE INVENTION

Figure 1:
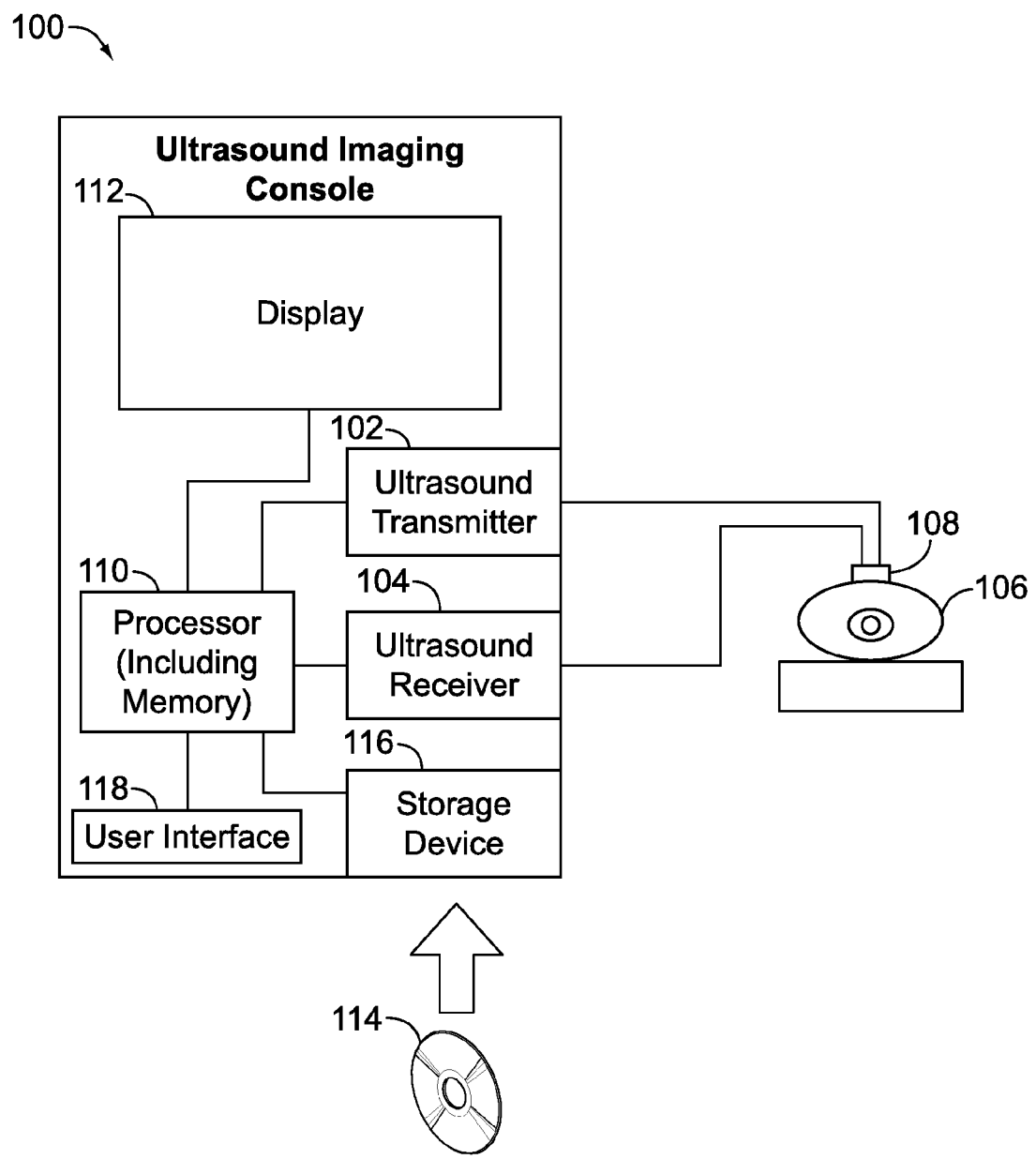
FIG. 1 illustrates a block diagram of an ultrasound imaging system that is formed in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

At least one embodiment disclosed herein makes use of methods for automatically adapting a deformable model to structures. In some embodiments, the methods may be computationally efficient. For example, the structure may be a left ventricle, a right ventricle, left ventricle outflow tract, and/or other cardiac structure. In another example, the structure may be another structure within the body or other object for which a set of standardized views are to be generated.

One method is described in U.S. patent application No. 11/775,903, filed Jul. 11, 2007, entitled "Method for Real-Time Tracking of Cardiac Structures in 3D Echocardiography", assigned to the same Applicant and herein incorporated by reference in its entirety. The Ser. No. 11/775,903 patent application relates to a method of tracking motion and shape changes of a deformable model that is fitted to edges in volumetric image sequences. The method utilizes an extended Kalman filter to estimate the position, orientation and deformation parameters of a deformable model. The shape and position of the deformable model is first predicted for each new frame, using a kinematic model. Edge detection is then performed in proximity to this model. The edge detection is done by searching for edges perpendicular to the model surface at regularly spaced locations across the model. The determined distances between the predicted and measured edges for the deformable model are treated as measurements to a least squares algorithm, such as a Kalman filter. The distance measurements are coupled with associated measurement noise values, which specify the spatial uncertainty of the local edge detection. Model parameter sensitivities with respect to the edge measurements are calculated for each edge-detection point. The sensitivities are combined with the edge measurements. The measurement data is subsequently summed together in the information space, and combined with the prediction in a Kalman filter to estimate the position and deformation parameters for the deformable model.

Another method is described in U.S. patent application Ser. No. 12/050,715, filed Mar. 18, 2008, entitled "Methods for Using Deformable Models for Tracking Structures in Volumetric Data", assigned to the same Applicant and herein incorporated by reference in its entirety. The Ser. No. 12/050,715 patent application relates to a computerized method for tracking of a 3D structure in a 3D image including a plurality of sequential image frames, one of which is a current image frame. The method includes representing the 3D structure being tracked with a parametric model with parameters for local shape deformations. A predicted state vector is created for the parametric model using a kinematic model. The parametric model is deformed using the predicted state vector, and a plurality of actual points for the 3D structure is determined using a current frame of the 3D image, and displacement values and measurement vectors are determined using differences between the plurality of actual points and the plurality of predicted points. The displacement values and the measurement vectors are filtered to generate an updated state vector and an updated covariance matrix, and an updated parametric model is generated for the current image frame using the updated state vector.

The above incorporated patent applications may utilize a Kalman filter tracking framework to perform fitting of a model to image data. The Kalman filter tracking framework is computationally efficient, that is, the models are updated or fitted to the image data in a single iteration. Therefore, the fitting may be accomplished in real-time or near real-time. It should be understood that other fitting methods may be used to implement at least one embodiment of the present invention, such as, but not limited to, other methods utilizing a least-squares method. Other fitting methods may be used that are capable of fitting the models to the image data in a single iteration or several iterations, allowing the fitting to occur in real-time or near real-time. In another embodiment, other fitting methods and algorithms that do not operate in real-time or near-real time may be used to fit the models to cardiac structures or other structures.

FIG. 1 illustrates a block diagram of an ultrasound imaging system 100 that is formed in accordance with an embodiment of the present invention. Ultrasound imaging system 100 includes an ultrasound transmitter 102 and an ultrasound receiver 104 configured to receive reflected ultrasound radiation reflected from a region of interest of an object 106 and to convert received ultrasound radiation into image data. Object 106 may be, for example, a medical patient, and the region of interest may, for example, include the heart of the patient. To emit ultrasound radiation into object 106 and to receive reflected ultrasound radiation therefrom, an ultrasound probe 108 is used to obtain successive frames of image data. Ultrasound imaging system 100 also includes a processor 110 configured to analyze the image data, and a display 112 configured to show results from the analysis of the image data. The processor 110 may be a module comprising a computational/logic engine (e.g., a microprocessor or CPU) together with memory, not shown separately in FIG. 1. A user interface 118 may be provided to allow the user to input data, select images, adjust and refine image data and imaging parameters, and the like. The user interface 118 may be any known input device, including, but not limited to, a keyboard, a trackball, mouse, touch screen, toggle switches, sliders, and buttons.

In some embodiments of the present invention, a storage device 116 is configured to read instructions from an external medium or media 114 such as CD-ROM, DVD, floppy disks, or other types of machine readable media known in the art. Instructions on medium or media 114 are configured to instruct ultrasound imaging system 100, for example, via processor 110, to perform a method embodiment of the present invention.

Some embodiments of the present invention need not necessarily be implemented using an ultrasound imaging system. A subset of the system shown in FIG. 1 is adequate for some embodiments. For example, a computer comprising a processor, memory, and display is suitable for implementing many embodiments of the present invention. In some embodiments the computer may be sufficient provided a suitable method is available for transferring image data from an imaging system, such as ultrasound imaging system 100 of FIG. 1. In other embodiments the transferring of the image data may be accomplished in real-time. Furthermore, the imaging system need not be an ultrasound imaging system or a medical imaging system, provided a sequence of image frames can be provided. In cases in which at least one embodiment is implemented in an ultrasound imaging system 100, the physical size of the imaging system is not restricted. For example, ultrasound imaging system 100 may be provided in a console format, a portable format, or a hand-held format.

Figure 2:
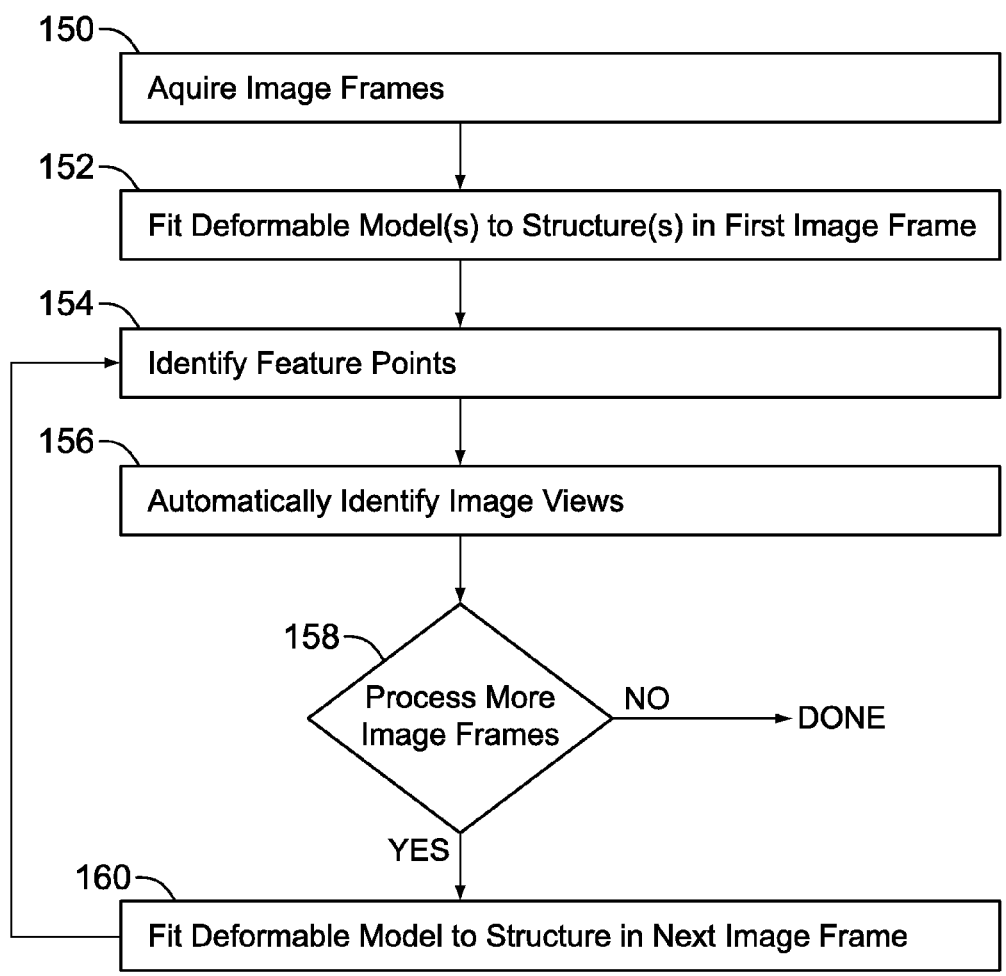
FIG. 2 illustrates a method for using a deformable model-based alignment algorithm to automatically create desired image views in accordance with an embodiment of the present invention.

FIG. 2 illustrates a method for using a deformable model-based alignment algorithm to automatically create desired image views. The term "image view" is a general term that may be used to refer to 2D slices, such as 2D slices from volumetric images, volumetric slices, volume renderings, such as a rendering of a heart valve or other desired anatomy, anatomic M-mode images, curved anatomic M-Mode images, time-motion curves (e.g. displacement, velocity, strain rate, strain, torsion, and the like), or any other extracted image view or representation or visualization technique that may be used when evaluating and/or comparing image data.

Image views may also refer to imaging views that are corrected for displacement, scaling and/or rotation, which may be a result of the alignment as discussed below. For example, short-axis slices that are corrected for out-of-plane motion (e.g. displacement during the heart cycle) may be created. One or more such corrected slices may be extracted from multiple images.

At 150, in some embodiments, the system 100 may acquire a sequence of N image frames. In some embodiments the image frames may include volumetric image data or may be referred to as a three-dimensional (3D) dataset. In one embodiment, the 3D dataset may include grayscale data, scalar grayscale data, parameters or components such as color, displacement, velocity, temperature, material strain or other information or source of information that may be coded into an image. The image frames may be acquired over the duration of the cardiac cycle, for example. The number N of image frames may vary from patient to patient and may depend upon the length of the individual patient's cardiac cycle as well as the frame rate of the imaging system 100.

In one embodiment, previously acquired images may be used to guide the user during the acquisition to acquire image frames that have approximately the same probe orientation. The probe orientation is the relative orientation of the probe 108 with respect to the anatomy of interest, such as the heart. The probe orientation is user dependent and may vary based on a user's knowledge, experience, technique, equipment available, as well as other factors. Additionally, different parts of the heart (or other anatomy) may be imaged, and the image volume may be rotated due to the probe 108 being rotated, such as by 90 or 180 degrees.

Probe orientation is relevant for studies such as stress echocardiography (stress-echo), where both rest and stress images are oriented approximately the same, that is, the same part of the heart is imaged with no relative rotation. For example, to acquire an apical four chamber view the probe 108 may be oriented by imaging between a patient's ribs and pointing along the direction of the left ventricle long axis, that is, approximately through the apex and through the middle of the mitral valve, and rotated so that a slice through the right and left ventricles and the right and left atria is displayed on the display 112.

Figure 12:
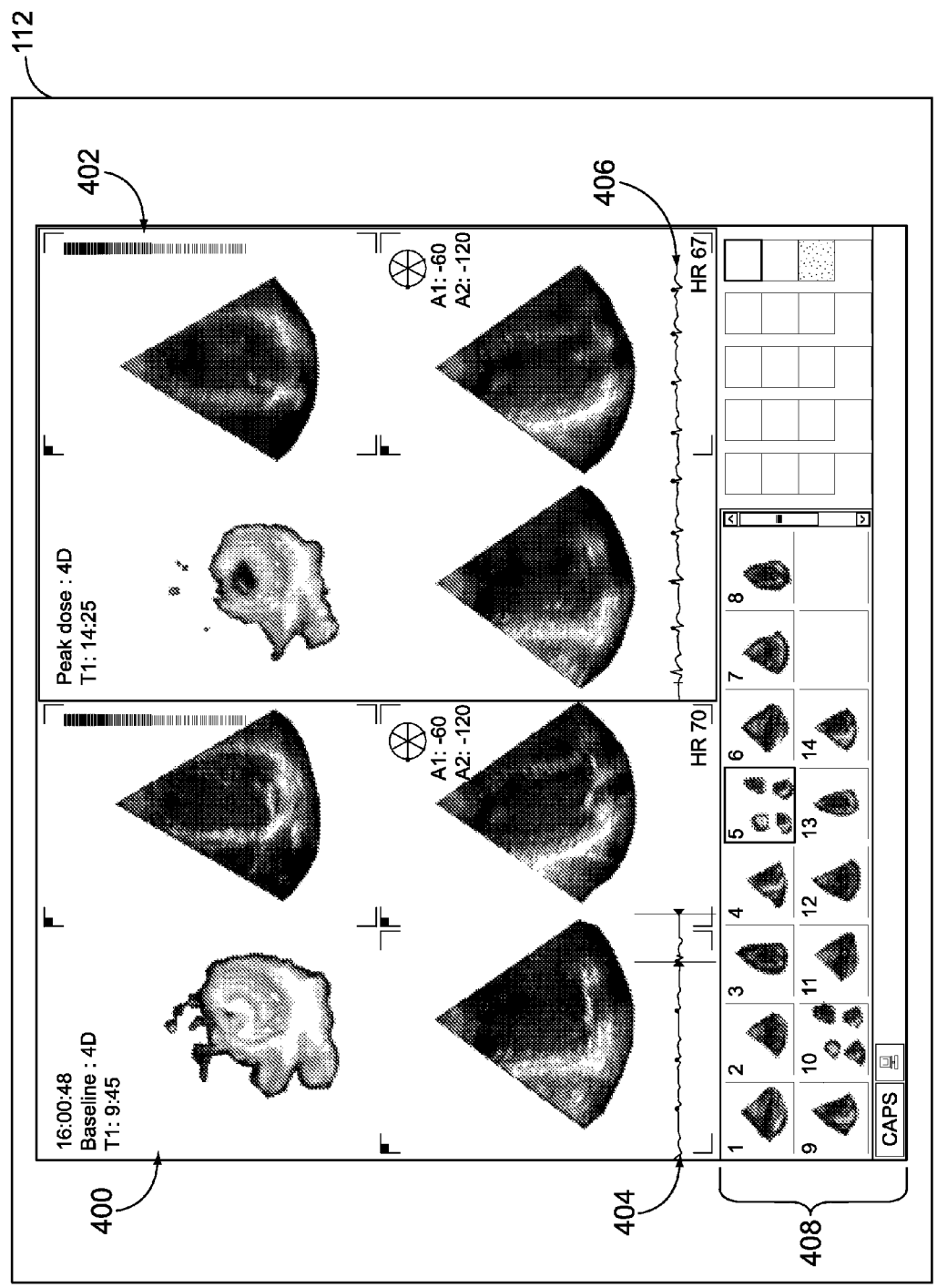
FIG. 12 illustrates a comparison of cardiac images that may be used to guide a user to adjust a probe orientation during acquisition in accordance with an embodiment of the present invention.

Viewing the previously acquired images on the display 112 simultaneously with the current image data helps the user to align images during acquisition. FIG. 12 illustrates a comparison of cardiac images that may be used to guide the user to adjust the probe orientation during acquisition so that the newly acquired images are aligned with reference images. Previously acquired reference images 400 are shown side-by-side with live images 402. Although four different images are shown in each of 400 and 402, it should be understood that one or more than one image may be used. In one embodiment, the reference images 400 may be previously acquired baseline images while the live images 402 are the stress images. In another embodiment, the reference images 400 may be stress images while the live images 402 are baseline images or images at other stress levels. The images may be from the same examination or a different examination. In one embodiment the reference images 400 may be from another patient, providing a general image to guide the user to acquire images at a specific probe orientation. In addition, the images 400 and 402 may be still images or cine-loops or other movie clip capturing movement of a moving object. Other information such as associated ECG traces 404 and 406 may be shown on the display 112, as well as images 408 or other indication that may identify location within the heart cycle.

The probe orientation may be based on a protocol that defines the order of the images and the relation between the images. Therefore, the user may be instructed to acquire a set of image frames at a first probe orientation, and then one or more additional sets of image frames may be acquired using different probe orientations. In another embodiment, imaging parameters such as geometry, frequency, frame rate, gain and the like may be automatically set so that baseline and any associated stress images are acquired using the same acquisition parameters, thus guiding the user to acquire images that are approximately equally aligned.

At 152, the processor 110 fits one or several deformable models to structures, such as a left ventricle, right ventricle, and/or left ventricle outflow tract, in the first image frame. In one embodiment, to accomplish the fitting of the left ventricle, tracking may be performed using a Kalman filter framework to segment the endocardial wall, using a deformable Doo-Sabin subdivision model. Similar fitting may be accomplished with deformable models for the right ventricle and left ventricle outflow tract. The tracking of multiple deformable models with respect to each other is discussed further below in FIGS. 8 and 9.

In some embodiments, because the tracking framework is computationally efficient, the fitting may be accomplished in real-time, as the image frames are being acquired. In another embodiment, the fitting may be accomplished on image data that has previously been acquired. For example, the image data may be acquired on the system 100, then transferred to and processed on a different system, or may be processed on the system 100 any time after the acquisition is complete.

In some embodiments, additional information may be used as an input to initiate the fitting which may thus increase the robustness of the fitting. Although in most cases the orientation of the probe 108 relative to the object under investigation may be determined by the alignment algorithm, in some examinations images may be acquired with a known probe orientation. Therefore, the knowledge of the probe orientation may be used as an input into the alignment algorithm, such as to initialize the model(s) for alignment of the image.

In another embodiment, the additional information used as an input to initiate the fitting may be based on previously acquired image data that has approximately the same probe orientation relative to the object under investigation. For example, the resulting alignment of one image may be used to initialize the model for alignment of another image. The alignment of the images is important in such studies as stress-echo so that like slices may be displayed and compared between the stress and rest images. The images may be from the same study (e.g. following a protocol that specifies the acquisition of images at rest and then at one or more levels of stress) or from different studies (e.g. two different protocols that may be, for example, acquired on different dates or at different times).

Therefore, the fitting for the different image datasets is approximately the same. For example, if the current study being processed is a stress cardiac study, data relating to the deformable models used when fitting the same patient's rest cardiac study may be used to increase the robustness of the fitting. For example, using information from a fitted model from rest to initialize model fitting in stress (or vice versa) may result in a better initialization than starting with an average model in the center of the image. In various embodiments, the previously acquired images may be images from the same patient acquired in a previous examination, images from the same patient and the same examination, or even images from another patient.

In stress-echo, for example, baseline images are typically acquired at low, or resting, heart rate. Therefore, the temporal image resolution relative to the heart rate is better than images acquired at a stressed, or higher, heart rate. For example, acquiring twenty frames per second at sixty heart beats per minute may result in better temporal image resolution compared to acquiring twenty frames per second at 180 heart beats per minutes, as the latter results in much larger myocardial movement between frames. Therefore, in some embodiments it may be desirable to use data associated with the baseline images when processing the stress images.

Even though the user may utilize previous images to increase the similarity between the probe orientations between acquisitions, some differences may exist. For example, when acquiring the stress images the user may have less time to adjust the probe 108 to the desired imaging location. Therefore, the algorithm may use the fitted models to improve the image alignment such that the images from different studies display or are based on the same anatomical structures.

Relating to the fitting, FIG. 3 illustrates a Doo-Sabin subdivision model 180 enclosed in a wire frame mesh 182 that shows a plurality of control vertices 184. For example, 34 control vertices 184 may be modeled in such a way that the mesh 182 may be accurately fit to the endocardial surface. Tracking is fully automatic, and may be initialized by placing a model with average shape in the center of the image sector and/or by the input(s) discussed above. Edge-detection measurement is performed in each image frame to detect the endocardial wall in search normals distributed evenly across the surface. Parameters for the shape of the model are combined with parameters for global translation, rotation and scaling to form a state-space representation. A Kalman filter may be used to assimilate all edge-detection measurements, and a Bayesian least-squares estimate of the model may be computed based on both edge measurements and predictions from a kinematic model.

Returning to FIG. 2, at 154 the processor 110 identifies feature points or landmarks from the segmented model. The feature points may be, for example, predefined points that identify apex and base, or the top and bottom, respectively, on a left ventricle model. For example, the apex may correspond to a point at a top 186 of the model 180 and the base may correspond to a center or approximate center of a bottom 188 of the model 180. It should be understood any other predetermined points may be used, such as model centroids, moments/central axis and the like. In addition, predetermined points may be extracted from other models, such as an apex, base or any other predetermined point in a right ventricle model, predetermined point(s) in a model of the left and/or right atria, predetermined point(s) in the model of the left ventricle outflow tract, or other points within other models of other structures of interest.

FIG. 4 illustrates exemplary segmented intersection slices at end diastole (ED) 190 and end systole (ES) 192 that have feature points identified thereon. Apex 194 and base 196 have been identified in the ED slice 190 from which the apex-base long-axis (LA) line 202 may be extracted. Apex 198 and base 200 are also identified in the ES slice 192, and the apex-base LA line 204 may be extracted. Apex 194 and apex 198 are not located at the same position and base 196 and base 200 are not located at the same position. The apex-base LA line 204 reflects a shorter distance between the apex 198 and base 200 compared to the apex-base LA line 202. This difference in distance represents the out-of-plane motion that may be experienced in short-axis slices during the heart cycle.

Returning to FIG. 2, at 156 the processor 110 may automatically identify image views. In some embodiments, knowledge about similar orientation between image views in a previously acquired study may be used to identify image view in another study. For example, LV short-axis slices that are corrected for out-of-plane motion may be identified and displayed on the display 112. The LV short-axis slices as well as other different types of exemplary image views are discussed further below in detail. In some embodiments, additional dimensions, such as temperature, displacement, velocity, strain and the like, as discussed previously, may be included within the image views, such as by utilizing color coding or other indications.

At 158 the processor 110 determines whether any further image frames should be processed. If no, the method is complete and image views may be displayed on the display 112, saved to the storage device 116, and the like. If more image frames are to be processed, at 160 the processor 110 fits the deformable model(s) to the structure(s) in the next image frame, and the method returns to 154 to identify the feature point(s) in the model(s) based on the current image frame.

FIG. 5 illustrates an example of identifying short axis slices based on the feature points. A fitted model 210 is shown and apex 212 and base 214 have been identified by the processor 110. A plurality of short axis slices 216 are identified on the model 210 with respect to the feature points, the apex 212 and base 214. In one embodiment, the short axis slices 216 may be evenly spaced with respect to each other between the apex 212 and the base 214. FIG. 5 illustrates a single image frame of data. On each of the N image frames, the plurality of short axis slices 216 are defined based on the apex and base that are identified within the particular image frame. Therefore, the short axis slices 216 track the tissue and/or anatomical structures of the heart and thus the anatomy is consistent from frame to frame.

Figure 6:
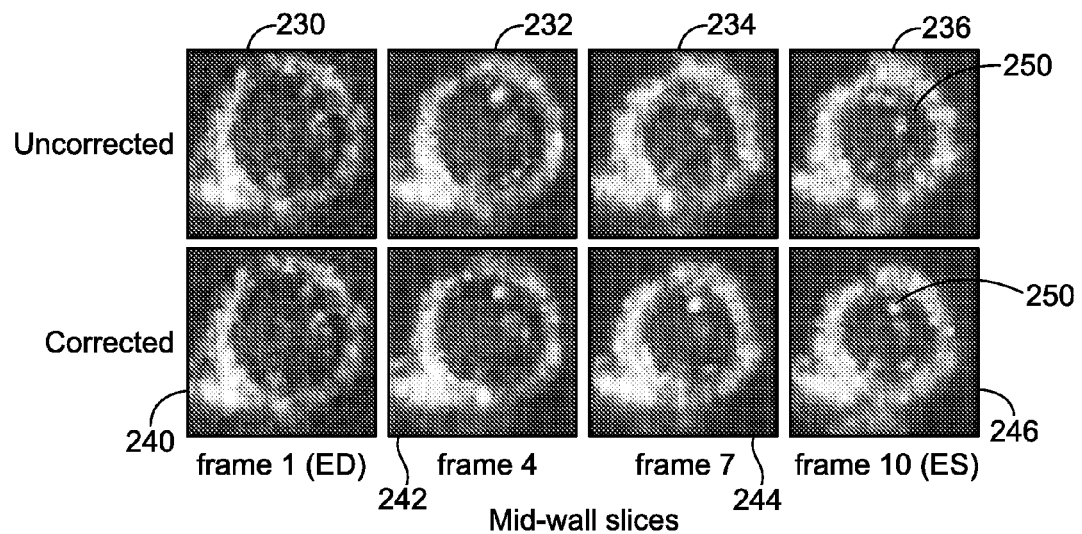
FIG. 6 illustrates a series of mid-wall image views that are based on the short-axis slices in accordance with an embodiment of the present invention.

FIG. 6 illustrates a series of mid-wall image views that are based on the short-axis slices. Image views 230 and 240 represent image data within the image slice corresponding to a first image frame at ED. Image views 232 and 242 represent image data within a fourth image frame, image views 234 and 244 represent image data within a seventh image frame, and image views 236 and 246 represent image data within a tenth image frame that corresponds to ES. The image views 230, 232, 234 and 236 are uncorrected, that is, the image views 230-236 are based on image data that has been processed by selecting feature points, such as apex and base, within one image frame, and applying the same feature points to the other N image frames. The image views 240, 242, 244 and 246 are corrected for out-of-plane motion caused by longitudinal shortening of the left ventricle, that is, the processor 110 has identified the feature points within each of the image frames and adjusted the locations of the short axis slices automatically prior to generating the image views 240-246. The corrected mid-wall image views 240-246 illustrate that the same part of papillary muscles 250 are tracked, while in the uncorrected mid-wall image views 230-236, the papillary muscles 250 move in and out of the image views 230-236.

Figure 7:
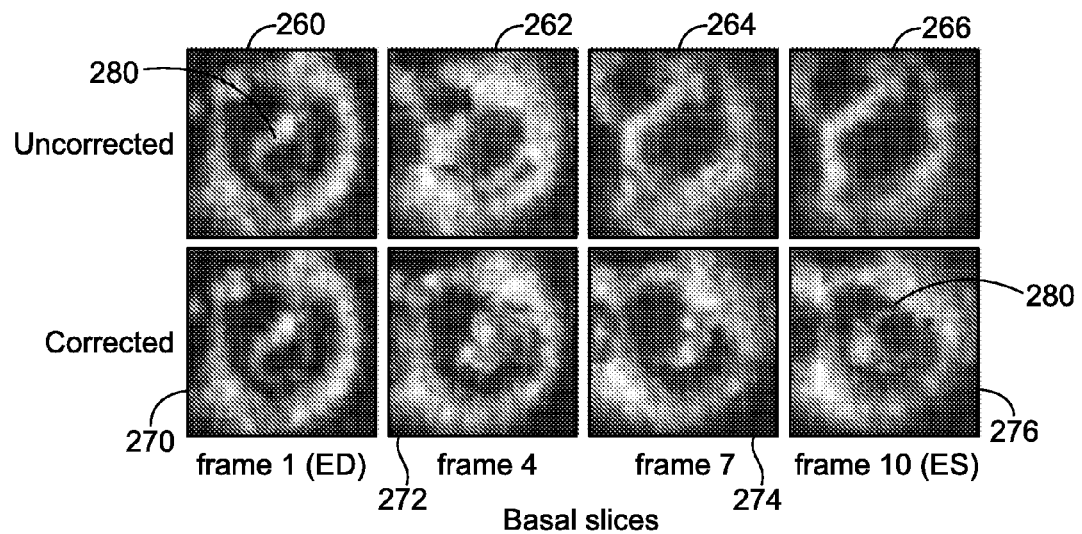
FIG. 7 illustrates a series of basal image views that are based on the short-axis slices in accordance with an embodiment of the present invention.

FIG. 7 illustrates a series of basal image views that are based on the short-axis slices. Similar to FIG. 6, image views 260 and 270 represent image data within a first image frame corresponding to ED. Image views 262 and 272 represent image data within a fourth image frame, image views 264 and 274 represent image data within a seventh image frame, and image views 266 and 276 represent image data within a tenth image frame that corresponds to ES. Again, image views 260, 262, 264 and 266 are uncorrected, based on feature points that have been identified within only one image frame within the series of N image frames. The images views 270, 272, 274 and 276 are corrected for out-of-plane motion, wherein the feature points have been identified on each of the N image frames and the short-axis slices are based on the corresponding feature points. The corrected basal image views 270-276 illustrate that the mitral valve 280 is followed throughout the image views 270-276, while the uncorrected basal image views 260-266 display the atria during systole.

In some embodiments, automatic alignment of some standard views may be accomplished by fitting several coupled deformable models to cardiac structures. The same computationally efficient tracking framework may be used as was discussed previously. The tracking framework may use an extended Kalman filter to perform temporal predictions, and edge-detection measurements from each model may be assimilated to compute a Bayesian least-squares fitting of the models in a non-iterative fashion. Feature points may then be extracted from the fitted models and used as a basis for the extraction of aligned standard views.

To generate some standard views using automatic alignment, information about both the ventricular long-axis and the circumferential orientation of the heart may be needed. In some cases, circumferential information extracted from the LV model alone may not be sufficient as the circumferential information is based solely on the asymmetrical properties of the shape, which can vary between subjects and depend upon pathology. Therefore, the coupling of two or more deformable models may be used to simultaneously track several cardiac structures. By computing the angle between the models for the different structures, a more reliable assessment of orientation may be accomplished.

In one embodiment, to enable detection of both of the long-axis and circumferential orientation, an LV model may be coupled with a sail-like structure for the inferior right ventricular (RV) wall. In another embodiment, a tube-line structure for the left ventricular outflow tract (OT) may be coupled together with the LV model and the sail-like structure. A deformable Doo-Sabin subdivision surface may be used as the LV model as previously discussed. For the RV, the inferior RV wall may be selected as this is the part of the RV that is usually most visible, compared to the anterior wall that may suffer from drop-out. All models may share a global transform for translation, rotation and scaling. The outflow tract model may also additionally be connected to a hinge transform (H), which allows the model to rotate to adapt to inter-subject differences in anatomy for the outflow tract.

Figure 8:
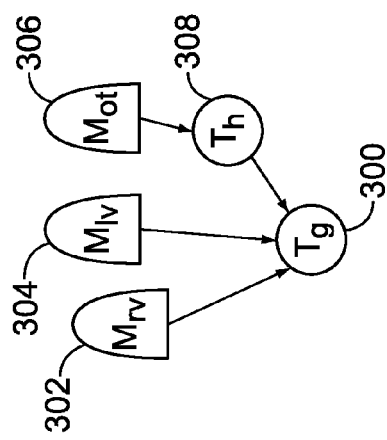
FIG. 8 illustrates how multiple models may be arranged in relationship to one another in a tracking hierarchy in accordance with an embodiment of the present invention.

FIG. 8 illustrates how the models may be arranged in relationship to one another in a tracking hierarchy. Global transform $T_g$ 300, RV sail $M_{rv}$ 302, LV model $M_{lv}$ 304, LV outflow tract $M_{ot}$ 306 and hinge transform $T_h$ 308 are shown. A state-space representation of the tracking hierarchy can be constructed by concatenating the parameters from all transforms and models into a state vector. The RV sail and outflow tract cylinder do not have any shape parameters and are only affected by their associated transforms, so the concatenated state vector becomes:

$$X = [X_g^T X_{lv}^T X_h^T]^T$$

Although not shown in FIG. 8, knowledge, such as the knowledge based on a previously acquired series of images or knowledge related to the orientation of the probe 108 as previously discussed, may be input to the global transform 300. In one embodiment, a user may input parameters with the user interface 118, such as the current orientation of the probe 108 that may be used by the alignment algorithm to better align the models. In another embodiment, knowledge may be used from a previously acquired series of images, such as the rest images, to provide input for processing of the stress images, and may also be used to update global parameters such a rotation.

Figure 9:
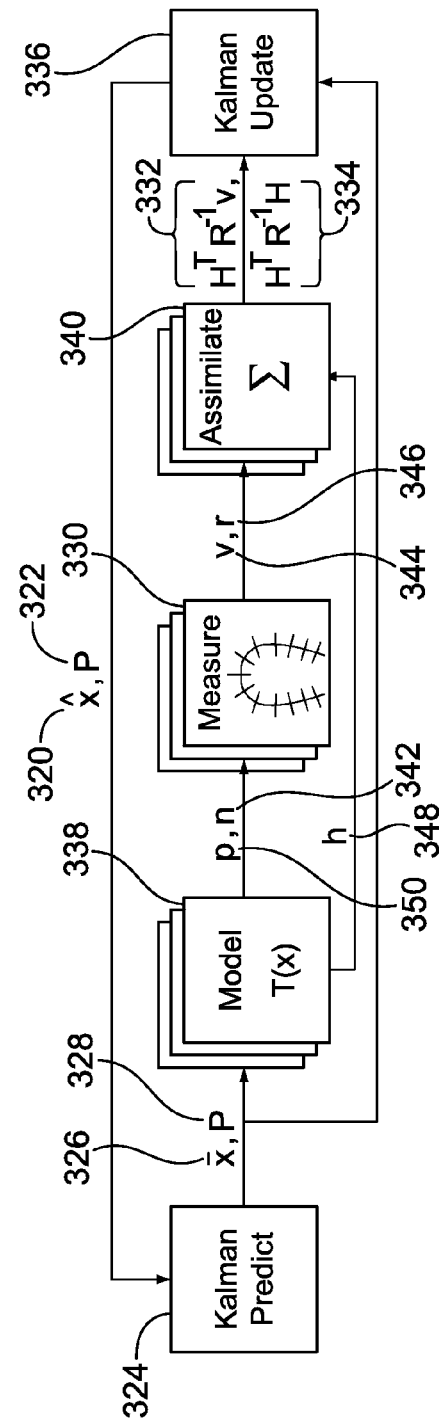
FIG. 9 illustrates an exemplary Kalman tracking framework including tracking hierarchy in accordance with an embodiment of the present invention.

FIG. 9 illustrates an exemplary Kalman tracking framework including tracking hierarchy. As illustrated in FIG. 9, state vector 320 and covariance matrix 322 for previous image frames are used in prediction step 324 to create a predicted state vector 326 and a predicted covariance matrix 328. As described below, the predicted state vector 326 and predicted covariance matrix 328 are utilized with the measurement step 330 to generate an information vector 332 and an information matrix 334. The information vector 332 and the information matrix 334 are used in updating step 336.

Kinematic models are used to predict contour states between successive image frames. Such models act by utilizing prior knowledge, yielding both a prediction for the state vector and the covariance matrix, specifying prediction uncertainty. The prediction can then be used as a starting point for more accurate refinements, called updates, where the prediction is combined with measurements from the current frame to form more accurate estimates.

Therefore, at the prediction step 324, temporal prediction of the composite state vector:

$$\overline{X}_{k+1} = f(\hat{X}_k, X_0)$$

may be based on the updated state from a previous frame and a prediction function $f$, with an associated increase in the covariance matrix 322, to generate a predicted state vector 326 and covariance matrix 328. In one embodiment, the temporal function may be a linear auto-regressive model.

As shown in FIG. 9, there are three boxes stacked with respect to each other for model step 338, the measurement step 330, and assimilate step 340. Each of the boxes refers to a different deformable model, and therefore in one embodiment there may be two models while in another embodiment there may be more than three models. The three models that are used in the example are shown in FIG. 8, that is, the RV sail 302, LV model 304 and the combination of the LV outflow tract 306 and the hinge transform 308. Therefore, the model step 338, measurement step 330 and assimilate step 340 in the tracking hierarchy are performed independently for each model.

At the model step, the processor 110 may evaluate surface points p 350, normal vectors n 342 and Jacobian matrices J for all models in the tracking hierarchy, based on the predicted state vector 326. At the measurement step 330, the processor 110 may detect normal displacement measurements v 344, measurement noise r 346 and measurement vectors h 348 wherein h=$n^T$J, based on edge detection in the image volume, relative to surface points from each of the predicted models. At the assimilate step 340, the processor 110 assimilates measurement results from each model by summing the results in information space, such as:

$$H^T R^{-1} v = \Sigma_i h_i r_i^{-1} v_i, H^T R^{-1} H = \Sigma_i h_i r_i^{-1} h_i^T$$

At the updating step 336, the processor 110 computes an updated state estimate, based on the prediction and measurement information, such as:

$$\hat{x}_k = \overline{x}_k + \hat{P}_k H^T R^{-1} v_k, \hat{P}_k^{-1} = \overline{P}_k^{-1} + H^T R^{-1} H$$

Tracking can be performed fully automatically, and in one embodiment, may be initialized by positioning a model with average shape in the center of the image sector. In other embodiments, other initializing data may be used based on user input, other images, input from a protocol, and the like. Edge-detection measurements are performed in each frame to detect the endocardial wall in search normals distributed evenly across the surface. Parameters for the shape of the model are combined with parameters for global translation, rotation and scaling to form a state-space representation of the segmentation problem.

The processor 110 may then identify feature points from the coupled, fitted models that may be used to generate standard apical and short-axis slices. As discussed previously with the single model, the short-axis slices are automatically updated after tracking in each frame to correct for out-of-plane motion caused by longitudinal shortening of the LV.

During tracking, feature points from the apex and base of the LV model are extracted from the segmented model after fitting in each frame. This is similar to the identification of the feature points as discussed in 154 of FIG. 2. Therefore, evenly distributed short-axis slices orthogonal to the apex-base long-axis may be generated as discussed previously and illustrated in FIG. 5.

In addition, angles and/or orientation between feature points on the LV model, the RV sail and outflow tract cylinder are also computed based on each of the N image frames to infer circumferential orientation of the heart. By way of example only, a vector may be created from the LA line 202 (as shown in FIG. 4) to each of the other structures (e.g. the RV sail and the outflow tract cylinder). The vectors are orientation dependent. The circumferential orientation may then be used to automatically generate standard apical 4-chamber, 2-chamber and long-axis views centered through the apex-base long-axis vector.

Figure 10:
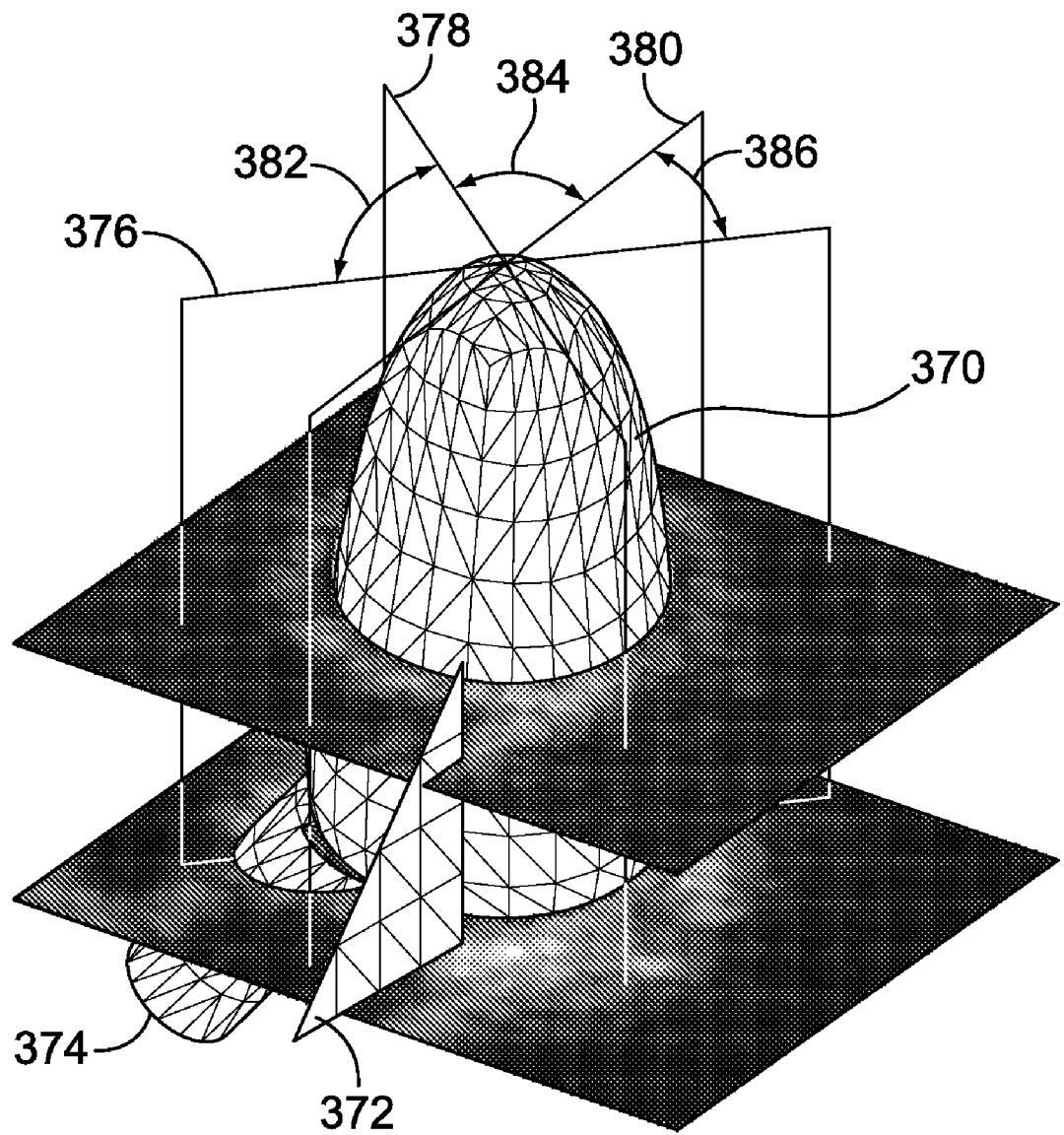
FIG. 10 illustrates an example of extraction of standard apical views based on feature points from coupled models in accordance with an embodiment of the present invention.

FIG. 10 illustrates an example of extraction of standard apical views based on feature points from the coupled models. In this example, an LV model 370, an RV sail model 372 and an LV outflow tract model 374 are coupled together.

As shown in FIG. 10, three slices 376, 378 and 380 corresponding to desired standard views may be positioned based on the angles and/or distances between the models. There is no assumption of a fixed angle between the slices 376, 378 and 380, and in some embodiments angles 382, 384 and 386 may be different with respect to each other. The angles 382, 384 and 386 may also be adaptive, based on relative distances or angles between the models, such as the distance between the RV sail and LV outflow tract models 372 and 374. Therefore, the angles 382, 384 and 386 between the slices 376, 378 and 380 are related, at least in part, to the angles between the models 370, 372 and 374. Additionally, other structure may be used to position and adjust the slices 376, 378, and 380, such as the papillary muscles, left and/or right atriums, right ventricle, and other structures, feature points and/or landmarks.

Figure 11:
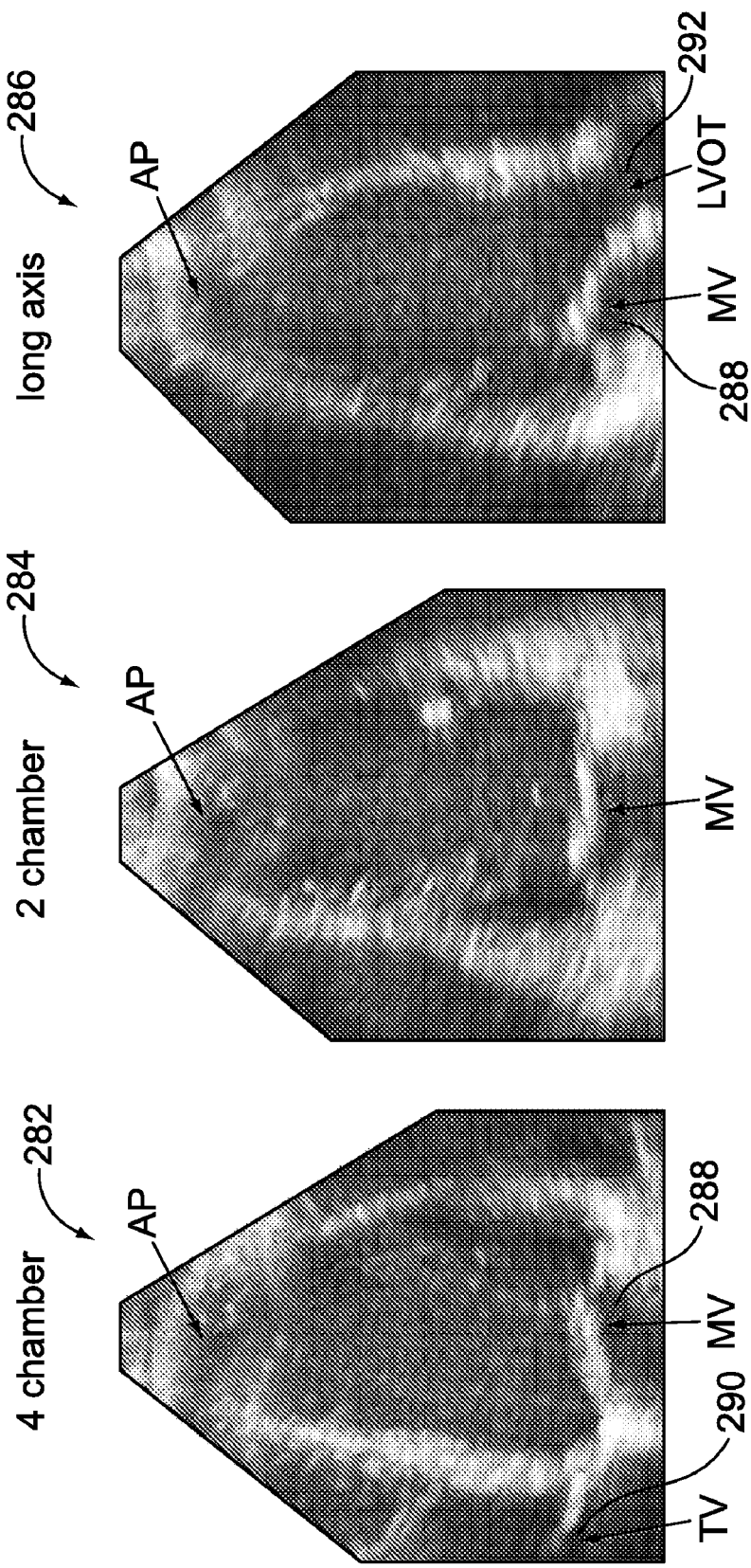
FIG. 11 illustrates three standard apical views formed in accordance with an embodiment of the present invention.

FIG. 11 illustrates three standard apical views, an apical four-chamber view 282, an apical two-chamber view 284, and an apical long axis view 286 corresponding to the three slices 376, 378 and 380. For example, automatic alignment of the N image views may ensure that mitral valve 288 and tricuspid valve 290 are both shown in each of the images corresponding to the four-chamber view 282. Also, automatic alignment of the N image views may ensure that the mitral valve 288 and outflow tract 292 are both shown in each of the images corresponding to the long axis view 286.

In some embodiments, the user may wish to manually adjust the alignment. For example, the automatic alignment may not correctly align the models and thus the resulting images may not include the desired image data. For example, the user may review the four chamber view and look for the presence of the left and right ventricles and the left and right atriums, as well as the mitral and tricuspid valves. If desired anatomy is not included within the view, the user may manually adjust the alignment.

In one embodiment, the processor 110 may display two or three long axis slices on the display 112. For example, the three long axis slices corresponding to the slices 376, 378 and 380 may be displayed on the display 112. One or more short axis slices, such as the images corresponding to the short axis slices 216 of FIG. 5 may also be displayed. The user may then use the user interface 118 to rotate, drag, translate, and/or otherwise adjust the image between the views to correct the alignment. In other words, the user may adjust or correct the alignment by rotating and translating the model relative to the object of interest. In another embodiment, the manual correction may involve rotation, translation, and/or scaling of the model relative to the object of interest. In yet another embodiment, the manual correction may involve adjusting the position of individual control vertices 184 (as shown in FIG. 3) relative to the object of interest.

In yet another embodiment, images, such as stress images, may be generated based on alignment information from the models used to generate the rest images. Therefore, the alignment algorithm may not be used to fit the models to the stress data. For example, parameters such as the size or length of the heart and coordinate or other location information may be known for valves and other anatomy. Therefore, it may be assumed that the geometry, size, position and orientation are the same for the rest and stress cases, even though the heart in the latter case beats faster. Accordingly, known alignment positions may be used to generate views such as the long axis, four chamber and two chamber. Model fitting may thus only be done on one recording, or one set of image frames, and then the parameters are applied to other sets of image frames. In some cases it may be desirable for the probe orientation for each of the image frames to be the same or approximately the same.

Aligned slices may be shown during post processing to compare images from different studies, sequences or video clips. The alignment may be needed, for example, if either the probe orientation is not correct relative to the left ventricle longitudinal axis (i.e. the probe main axis is not along the LV main longitudinal axis), or if the probe orientation is not equal between studies acquired at different stress levels. It should be understood that many different types of images may be generated, displayed and compared, and thus are not limited to those specific examples described herein.

Figure 13:
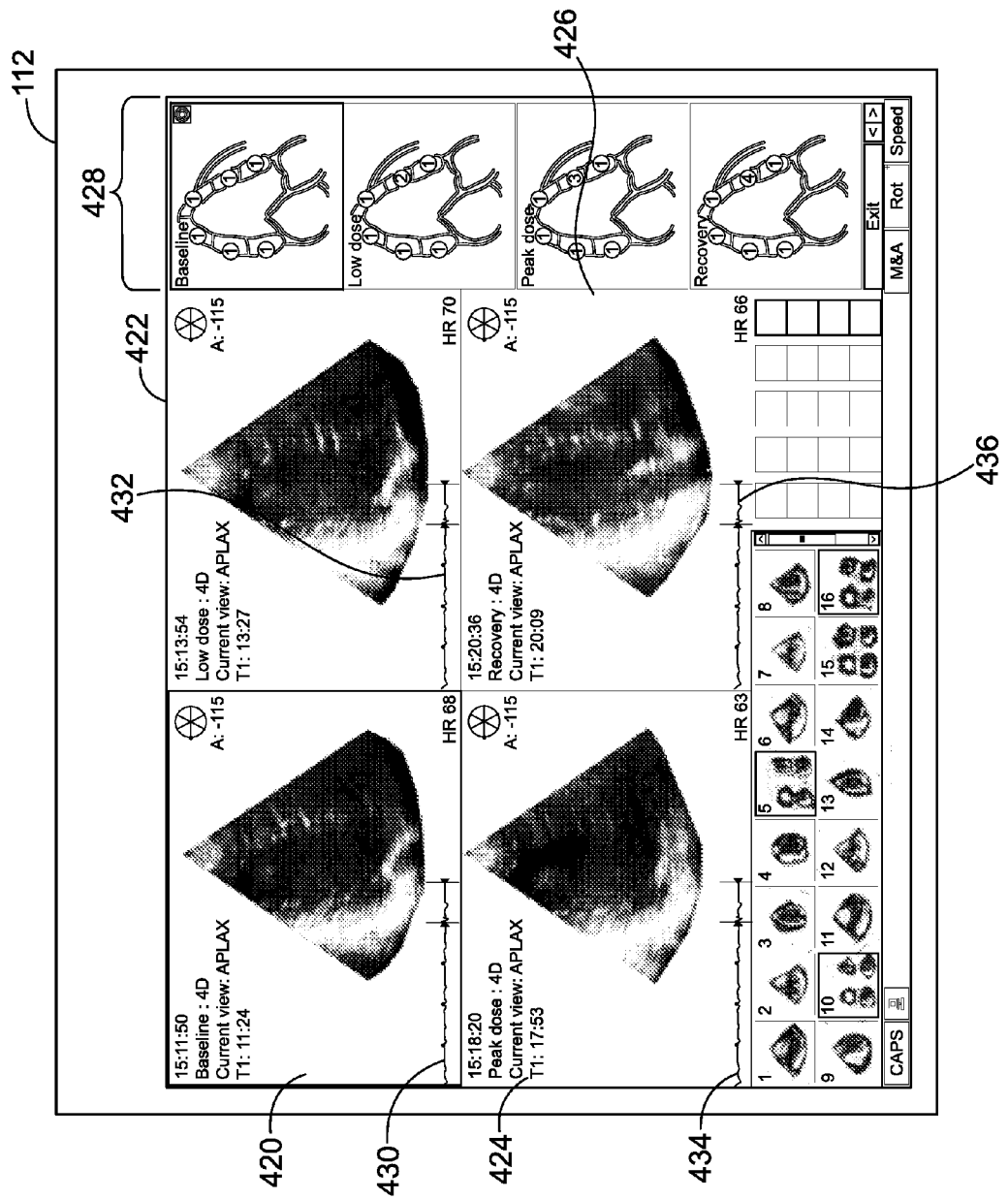
FIG. 13 illustrates post-processing of apical long-axis images from a stress-echo examination in accordance with an embodiment of the present invention.

FIG. 13 illustrates post-processing of apical long-axis images from a stress-echo examination. In this example, the stress-echo examination included acquiring multiple sets of image frames at different levels of stress. A baseline image 420, low dose image 422, peak dose image 424 and recovery image 426 are shown together on the display. The images 420-426 have been extracted automatically from four different sequences of image frames. Wall motion scoring diagrams 428 are also shown, where the user may enter results of segmental wall motion analysis. Therefore, the user may be able to compare images that include the same anatomical data but that were acquired at different stress levels and/or times.

ECG traces 430, 432, 434 and 436 may also be displayed. For example, when the object of investigation (e.g. the heart) has a cyclic movement pattern, then image cine-loops or movies may be synchronized over time. When viewing images based on echocardiography, for example, both during acquisition and during post processing the images are synchronized by using the ECG signal or other detection means. Therefore, the systolic part of all the image cine-loops are displayed on the display 112 simultaneously and the diastolic parts are displayed simultaneously.

In another embodiment, one or more of the images 420-426 may be displayed with, and thus compared to, like images from the same patient that were taken at a different time, such as months apart, to another patient or to example normal images, for example.

Figure 14:
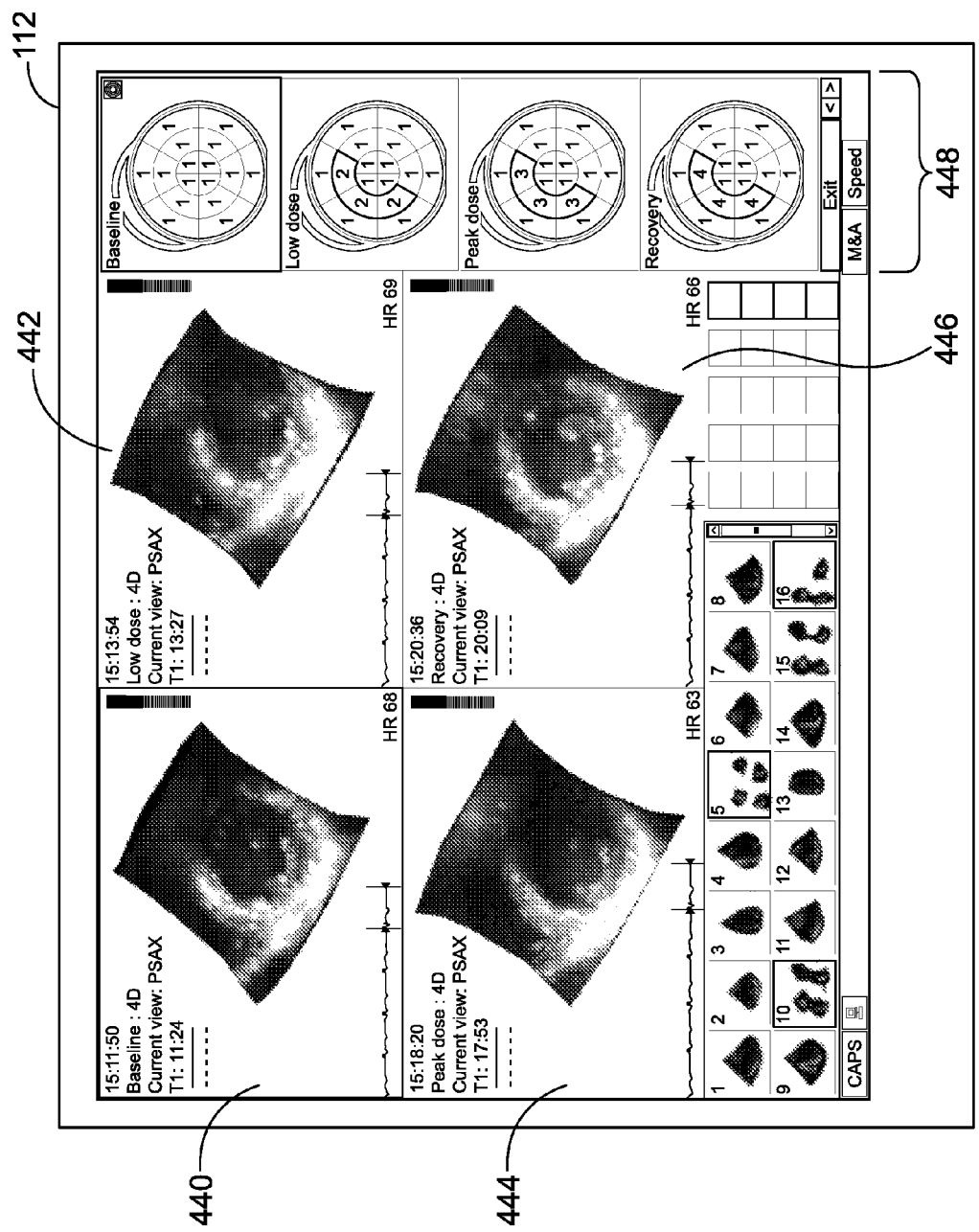
FIG. 14 illustrates post-processing of short-axis images from a stress-echo examination in accordance with an embodiment of the present invention.

FIG. 14 illustrates post-processing of short-axis images from a stress-echo examination. In this example the short-axis images are from mid level of the LV, although other positions may similarly be displayed. A baseline image 440, low dose image 442, peak dose image 444 and recovery image 446 are shown together on the display 112. The images 440-444 have been extracted automatically from four different sequences of image frames. Wall motion scoring diagrams 448 (i.e. Bulls-Eye diagrams for example, although others may be used) may also be displayed, allowing the user to enter the result of segmental wall motion analysis through the user interface 118.

A technical effect of at least one embodiment is using deformable model-based alignment to automatically create desired image views. In some embodiments the deformable model-based alignment may be computationally efficient. One model may be used to create the image views, or more than one model may be coupled together. In some embodiments, image views may thus be generated that display like anatomy over time, such as over a heart cycle. In another embodiment, image views of like anatomy from different sets or sequences of images frames may be generated and compared to each other.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for automatically identifying image views in a three-dimensional dataset, comprising:
    accessing with a processor a three-dimensional (3D) dataset comprising a plurality of image frames;
    fitting with the processor at least one deformable model to at least one structure within each of the image frames;
    identifying with the processor at least one feature point within each of the image frames based on the at least one deformable model; and
    displaying on a display at least one image view based on the at least one feature point.

2. The method of claim 1, wherein the fitting comprises fitting the at least one deformable model based on a Kalman filter.

3. The method of claim 1, wherein the at least one deformable model comprises at least one of a sail, a cylinder, a left ventricle model and a right ventricle model.

4. The method of claim 1, wherein the at least one image view comprises at least one of a four chamber view of a heart, a two chamber view of a heart, an apical long axis view of a heart, a short axis view comprising image data corresponding to a left ventricle within a heart, and a rendering of a heart valve.

5. The method of claim 1, wherein the fitting is accomplished in one iteration using a least-squares method.

6. The method of claim 1, wherein the method is performed in real-time during acquisition of image frames.

7. The method of claim 1, wherein the method is performed after the plurality of consecutive image frames are acquired.

8. The method of claim 1, wherein the identifying at least one feature point further comprises identifying an apex and a base of a cardiac structure in each of the plurality of consecutive image frames.

9. The method of claim 1, wherein the at least one deformable model comprises at least two deformable models and the at least one structure comprises at least two structures, the method further comprising identifying an orientation of the at least two structures to each other based on the at least two deformable models.

10. The method of claim 1, wherein the fitting is initialized based on a fitted model from a second plurality of image frames, and wherein the plurality of image frames and the second plurality of image frames were acquired with similar orientation.

11. The method of claim 1, further comprising displaying at least one corresponding image view simultaneously with the at least one image view, the at least one corresponding image view based on a second plurality of image frames.

12. The method of claim 1, further comprising adjusting the at least one image view based on input from a user interface to display a different portion of the dataset.

13. A system for automatically identifying image views in a three-dimensional dataset, comprising:
    a processor configured to:
        access a three-dimensional dataset comprising a plurality of image frames;
        fit at least two coupled deformable models to structures within each of the image frames;
        identify at least one feature point within each of the image frames based on at least one of the deformable models; and
    a display configured to display at least one image view based on the at least one feature point.

14. The system of claim 13, further comprising an ultrasound probe configured to acquire the plurality of image frames, the probe comprising a probe orientation with respect to at least one of the structures, the processor further configured to initialize the fit of at least one of the models based on the probe orientation.

15. The system of claim 13, further comprising an ultrasound probe configured to acquire the plurality of image frames, the display further configured to display at least one image view based on a different plurality of image frames simultaneously with the acquisition of the plurality of image frames.

16. The system of claim 13, wherein the processor is further configured to fit the models to the structures based on at least one of a probe orientation associated with the plurality of image frames, a probe orientation associated with a protocol, and information based on a fitted model from a second plurality of image frames that was acquired with a probe orientation that is substantially similar to the probe orientation used to acquire the plurality of image frames.

17. The system of claim 13, wherein the processor is further configured to determine an orientation between the at least two coupled deformable models, and wherein the at least one image view is further based on the orientation.

18. The system of claim 13, further comprising a user interface configured to accept input, the processor further configured to adjust the fit of at least one of the deformable models based on the input.

19. The system of claim 13, wherein the display is further configured to display at least one image view based on the plurality of image frames and at least one additional image view based on a different plurality of image frames, the at least one image view and the at least one additional image view comprising like anatomy.

20. The system of claim 13, wherein the at least one image view comprises at least one of a two-dimensional slice, a volumetric slice, a volume rendering, an anatomic M-mode image, a curved anatomic M-mode image, a time-motion curve, and an extracted image view based on the multi-dimensional dataset.

* * * * *